United States Patent
McMinn

(10) Patent No.: US 9,737,407 B2
(45) Date of Patent: Aug. 22, 2017

(54) PROSTHETIC COMPONENT

(76) Inventor: Derek James Wallace McMinn, West Midlands (GB)

( * ) Notice: Subject to any disclaimer, the term of this patent is extended or adjusted under 35 U.S.C. 154(b) by 0 days.

(21) Appl. No.: 13/822,888

(22) PCT Filed: Sep. 13, 2011

(86) PCT No.: PCT/GB2011/001338
§ 371 (c)(1),
(2), (4) Date: Mar. 29, 2013

(87) PCT Pub. No.: WO2012/035294
PCT Pub. Date: Mar. 22, 2012

(65) Prior Publication Data
US 2013/0184831 A1   Jul. 18, 2013

(30) Foreign Application Priority Data

Sep. 13, 2010 (GB) .................................. 1015143.9
Apr. 7, 2011 (GB) .................................. 1105939.1

(51) Int. Cl.
*A61F 2/32*   (2006.01)
*A61F 2/38*   (2006.01)
(Continued)

(52) U.S. Cl.
CPC .............. *A61F 2/3859* (2013.01); *A61F 2/30* (2013.01); *A61F 2/30734* (2013.01);
(Continued)

(58) Field of Classification Search
CPC ..................................... A61F 2/32; A61F 2/38
(Continued)

(56) References Cited

U.S. PATENT DOCUMENTS 3,685,058 A   8/1972   Tronzo
4,908,034 A   3/1990   Weightman et al.
(Continued)

FOREIGN PATENT DOCUMENTS

DE   3903438 A1   8/1990
EP   0457222 A1   11/1991
(Continued)

OTHER PUBLICATIONS

GB Combined Search and Examination Report under Sections 17 and 18(3) dated Nov. 15, 2010 and received Nov. 18, 2010 for Application No. GB 1015143.9 (6 pages).
(Continued)

*Primary Examiner* — Yashita Sharma
(74) *Attorney, Agent, or Firm* — Morgan, Lewis & Bockius LLP

(57) ABSTRACT

The invention relates to a prosthesis comprising a first component (10) and a second component (60), wherein the first and second components have respective inter-engaging parts (24,64) and wherein at least one of the first or second components comprises an anti-rotational element (32,66) configured to resist rotational movement between the inter-engaging parts and wherein the inter-engaging parts share an axis of rotation such that they are engageable in a plurality of relatively rotated positions and wherein the axis of rotation of the inter-engaging part of one of the first or second components is parallel to but offset from a central axis of said first or second component.

4 Claims, 10 Drawing Sheets

(51) Int. Cl.
*A61F 2/30* (2006.01)
*A61F 2/36* (2006.01)

(52) U.S. Cl.
CPC .... *A61F 2/3609* (2013.01); *A61F 2002/3054* (2013.01); *A61F 2002/30138* (2013.01); *A61F 2002/30299* (2013.01); *A61F 2002/30332* (2013.01); *A61F 2002/30344* (2013.01); *A61F 2002/30347* (2013.01); *A61F 2002/30367* (2013.01); *A61F 2002/30474* (2013.01); *A61F 2002/30553* (2013.01); *A61F 2002/365* (2013.01); *A61F 2002/3611* (2013.01)

(58) Field of Classification Search
USPC .... 623/20.35–20.36, 22.11–22.2, 22.4–23.14
See application file for complete search history.

(56) References Cited

U.S. PATENT DOCUMENTS

| | | | |
|---|---|---|---|
| 5,314,479 A | 5/1994 | Rockwood, Jr. et al. | |
| 5,405,403 A | 4/1995 | Mikhail | |
| 5,480,451 A * | 1/1996 | Grundei et al. | 623/22.43 |
| 5,653,764 A | 8/1997 | Murphy | |
| 8,088,169 B2 * | 1/2012 | Dorr et al. | 623/23.59 |
| 2007/0255420 A1 * | 11/2007 | Johnson | A61F 2/3601 |
| | | | 623/22.44 |

FOREIGN PATENT DOCUMENTS

| | | |
|---|---|---|
| EP | 0470778 A1 | 2/1992 |
| EP | 1872745 A2 | 1/2008 |
| FR | 2697996 A1 | 5/1994 |
| FR | 2763501 A1 | 11/1998 |
| FR | 2837695 A1 | 10/2003 |
| FR | 2889446 A1 | 2/2007 |

OTHER PUBLICATIONS

International Search Report and Written Opinion issued for International Application No. PCT/GB2011/001338 issued on Nov. 17, 2011 and mailed Mar. 5, 2012 (17 pages).

* cited by examiner

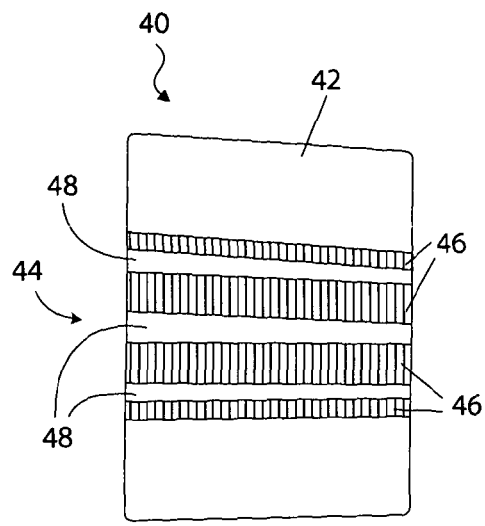 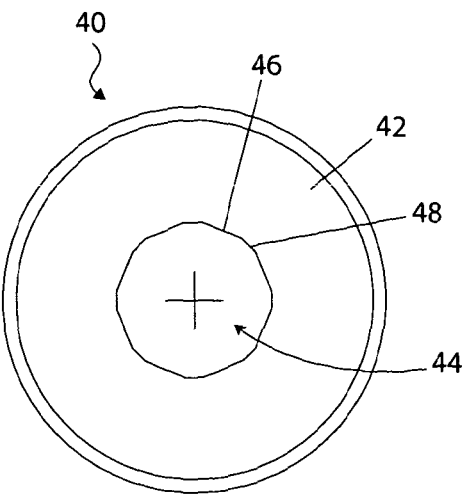
Fig. 2A  Fig. 2B
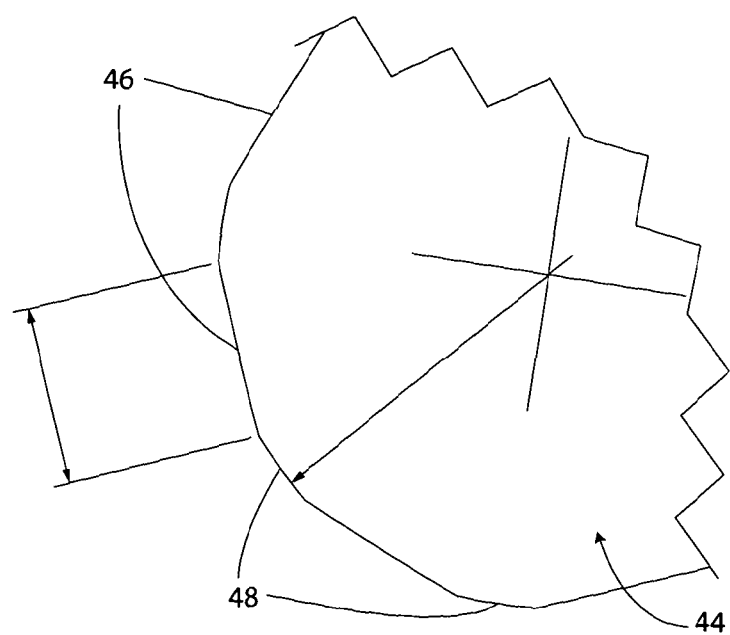
Fig. 2C

PROSTHETIC COMPONENT

RELATED APPLICATIONS

This application is a U.S. National Phase Application of PCT/GB2011/001338, filed Sep. 13, 2011, which claims priority to and the benefit of United Kingdom Patent Application No. 1015143.9, filed on Sep. 13, 2010, and United Kingdom Patent Application No. 1105939.1, filed Apr. 7, 2011, all of which are incorporated herein by reference.

FIELD OF THE INVENTION

The present invention relates to a prosthetic component. Particularly, but not exclusively, the invention relates to a prosthetic component for use in a Total Hip Replacement (THR) procedure.

BACKGROUND TO THE INVENTION

A THR prosthesis typically comprises a femoral stem component and a femoral head component. The stem commonly includes a conical element, extending from a neck of the stem, for engagement in a complementary recess within the femoral head.

The femoral head of a THR prosthesis is generally more expensive to manufacture than the stem and often come in a range of sizes to suit different patients. For example, heads are commonly provided with maximum diameters of 38 mm through to 58 mm, in increments of 2 mm. In addition, surgeons usually desire to have a range of head lengths available (e.g. −8, −4, 0, +4, +8 and +12 mm) for each head diameter. In this instance a head length of 0 mm denotes that which would result in the patient's leg length being the same as it was before the operation. Consequently, it is often necessary for hospitals to stock many different sizes of head when only one of these will be required for any given procedure.

In order to address this problem, prosthetic sleeves are often provided to fit over the conical element of the stein so that only one head of each diameter need be provided. The sleeves can be provided in different lengths (e.g. to provide head lengths of −8, −4, 0, +4, +8 and +12 mm) but without the expense of providing so many bespoke heads.

The sleeves are usually configured for a tight frictional fit onto the conical element and a similar frictional fit within the head recess.

Where ceramic components are used, the conical element is often adapted to minimize the risk of a brittle ceramic head from cracking or breaking when the conical element is inserted therein. Accordingly, the conical element may be provided with a series of circumferential grooves and ridges to reduce bursting stresses on the head. However, the grooves and ridges typically cause cavities to appear, in which fluid can nest, leading to crevice corrosion which can weaken the frictional fit between the components.

Today ridges and grooves are commonly machined into mating taper surfaces in hip prosthesis, even in metal only taper junctions, because they can help to even out stresses resulting from an imperfect matching of the mating surfaces. As above, the ridges and grooves are circular and are provided in planes that are orthogonal to the longitudinal axis associated with the taper. However, the two complementary sets of circular disposed ridges and grooves on the taper junction further reduce the frictional fit at the component interface.

It is therefore an aim of the present invention to provide a prosthetic component that ameliorates the afore-mentioned problems.

SUMMARY OF THE INVENTION

According to a first aspect of the present invention there is provided a prosthesis comprising a first component and a second component, the first and second components having respective inter-engaging parts and wherein at least one of the first or second components comprises an anti-rotational element configured to resist rotational movement between the inter-engaging parts and wherein the inter-engaging parts share an axis of rotation such that they are engageable in a plurality of relatively rotated positions and wherein the axis of rotation of the inter-engaging part of one of the first or second components is parallel to but offset from a central axis of said first or second component.

According to a second aspect of the present invention there is provided a prosthetic component configured for mating with another prosthetic component, the prosthetic component and the another prosthetic component having inter-engaging parts, wherein the prosthetic component comprises an anti-rotational element configured to resist rotational movement between the inter-engaging parts and wherein the inter-engaging parts share an axis of rotation such that they are engageable in a plurality of relatively rotated positions and wherein the axis of rotation of the inter-engaging part of the prosthetic component is parallel to but offset from a central axis of said prosthetic component.

The Applicant believes that when prosthetic implants encounter a high level of frictional torque at a bearing surface this can give rise to small rotational movements between other inter-engaging parts of the prosthesis, which can cause wear and corrosion. It is believed that this effect will not only occur in prosthesis having metal to metal bearing components but also in large-headed metal and polyethylene bearings, particularly at high loads and particularly where cross-linked polyethylene is employed.

Embodiments of the present invention address this problem by providing an anti-rotational element configured to resist rotational movement between the inter-engaging parts. Accordingly, aspects of the present invention provide prosthesis with a rotationally stable configuration. In addition, aspects of the present invention aim to minimise wear and corrosion of inter-engaging parts by increasing the resistance to rotational torque. Advantageously, embodiments of the invention also provide a means for altering the relative positions of the two prosthetic components due to the offset nature of one of the inter-engaging parts with respect to the component it is provided on. Accordingly, relative rotation of the inter-engaging parts, part to their engagement, results in relocation of the central axis of one of the components with respect to the other component. This allows the components to be arranged in a plurality of different positions to provide a required angle of inclination there-between. Furthermore, by arranging the axis of rotation of the inter-engaging parts to be parallel to but offset from the central axis of one of the components, we provide an asymmetrical component which extends further away from the inter-engaging parts in one direction than in the other. This permits the relative heights of the components to be adjusted by simply relocating the thickest portion of the asymmetrical component to a position in which the desired height is achieved.

The prosthesis may be configured for use in a joint replacement or resurfacing procedure. The prosthesis may be configured for use in a hip, knee, ankle, toe, shoulder, elbow, wrist, finger or other joint.

The inter-engaging parts may comprise a male part and a female part. The male and female parts may comprise complementary tapering surfaces. The male part may be constituted by a conical or frusto-conical element. The female part may be constituted by a conical or frusto-conical recess.

Two or more anti-rotational elements may be provided on one or both of the first and second components of the first aspect of the invention (and/or on the prosthetic component of the second aspect of the invention). The two or more anti-rotational elements may be connected or non-connected. For example, the two or more anti-rotational elements may be provided adjacent each other or spaced from each other. In particularly advantageous embodiments, the two or more anti-rotational elements may be circumferentially spaced apart around a curved surface (e.g. around a conical element or recess). This is advantageous because it can allow a standard replacement component (e.g. a femoral head with a plain conical recess) to be used on a prosthetic component of the present invention (e.g. a conical femoral neck comprising said anti-rotational elements) because the recess will still be able to mate sufficiently well with the remaining curved portions of the conical neck surface.

The anti-rotational element may comprise one or more planar mating surfaces (flats). In certain embodiments, a plurality of planar mating surfaces may be provided. The plurality of planar mating surfaces may be provided on a curved surface (e.g. a convexly curved surface) and may be disposed in a spaced relationship around the curved surface. The plurality of planar mating surfaces may be spaced equal distances apart. As mentioned above an advantage of maintaining portions of the convexly curved surface between the flats is that, if revision surgery is required, a standard replacement component (e.g. a femoral head with a conical recess) can still be used and will still mate sufficiently well with the curved portions of the surface.

In other embodiments, the plurality of planar mating surfaces may disposed adjacent each other but at different angles thereto (e.g. to form a pentagonal, hexagonal, heptagonal or octagonal cross-section).

More generally, the anti-rotational element may comprise one or more recessed mating surfaces (e.g. indents or cut-outs). The recessed mating surfaces may be in the form of channels, slots or grooves and may comprise straight and/or curved surfaces. In particular embodiments, the recessed mating surfaces may comprise concavely curved channels (e.g. forming deep part-circular or semi-circular grooves) and/or wedge-shaped channels (e.g. forming deep U or V-shaped grooves). In certain embodiments, a plurality of recessed mating surfaces (e.g. eight recessed mating surfaces) may be provided.

The plurality of recessed mating surfaces may be provided on a curved surface (e.g. a convexly curved surface) and may be disposed in a spaced relationship around the curved surface. The plurality of recessed mating surfaces may be spaced equal distances apart. As above, an advantage of maintaining portions of the convexly curved surface between the recesses is that, if revision surgery is required, a standard replacement component (e.g. a femoral head with a conical recess) can still be used and will still mate sufficiently well with the convexly curved portions of the surface.

The Applicant has found that, in practice, when the anti-rotational element comprises a plurality of non-connected flat (e.g. planar) surfaces, there is a risk that surgeons may insert the female part of the prosthesis (e.g. the sleeve or head) onto the male part of the prosthesis (e.g. neck cone) in a mal-rotated position (e.g. where the flat surfaces are not correctly aligned). However, the Applicant has also found that by replacing the planar surfaces with deeper recessed features such as channels, which may be concavely curved or wedge-shaped, the likelihood of the surgeon mal-rotating the sleeve on the cone is eliminated or at least greatly reduced.

In other embodiments, the plurality of recessed mating surfaces may be disposed adjacent each other.

The anti-rotational element may comprise one or more substantially longitudinal ridges, planar surfaces, recessed surfaces (e.g. grooves) or splines on one or both of the inter-engaging pans.

Circumferential ridges, grooves or splines may also be provided on one or both of the inter-engaging parts and may be configured for elastic and/or plastic deformation. The circumferential ridges, grooves or splines may be provided to reduce stresses between the first and second components, particularly, when ceramic components are employed.

In a particular embodiment, longitudinal ridges, grooves or splines may be provided on one of the first or second components and circumferential ridges, grooves or splines may be provided on the other of the first or second components. In this case, when the two components are impacted together, the tips of the ridges may deform, biting into each other and thereby improving torsional resistance.

Additionally or alternatively, the anti-rotational element may comprise an adhesive or friction-enhancing fluid. Such embodiments are advantageous in that the adhesive or friction-enhancing fluid may be permitted to fill any unwanted cavities in the inter-engaging parts so as to reduce the risk of other fluids entering those cavities and causing crevice corrosion. Moreover, the provision of an adhesive would help to improve the mechanical lock of the inter-engaging parts.

The anti-rotational element may be provided over substantially the whole or a portion of one or both of the inter-engaging parts. In certain embodiments, the anti-rotational element may be located in one half of the (or each) inter-engaging part.

At least one of the inter-engaging parts may be asymmetrical. For example, the centre the inter-engaging part on one of the first or second components may be off-set from the centre of the said first or second component. This is advantageous because it can allow the said component to be engaged in a number of different relative positions in order to suit different circumstances.

The first or second (prosthetic) component may be configured as a femoral stem, a femoral sleeve or a femoral head.

In certain embodiments, the first (prosthetic) component may be configured as a femoral stem and the second (another) prosthetic component may either be configured as a femoral sleeve or a femoral head, having an inter-engaging part configured for mating with a corresponding inter-engaging part of the femoral stem. Thus, aspects of the present invention may be employed in sleeved or non-sleeved THR prosthesis.

The femoral stem may comprise a neck from which the inter-engaging part extends. The inter-engaging part may comprise a substantially frusto-conical taper which is widest adjacent the neck.

The femoral sleeve may be constituted by a frusto-conical collar in which the inter-engaging part comprises a substantially frusto-conically tapered internal recess or passageway.

The anti-rotational element may be provided on one or both of the frusto-conical taper and the frusto-conically tapered recess or passageway. Accordingly, the innermost tapered surfaces of the prosthesis will be resistant to rotational torque such as that which may be caused by the presence of high frictional torque at the femoral head and ace-tabular cup bearing interface.

The femoral head may comprise a part-spherical bearing surface having an internal support comprising a substantially frusto-conically tapered internal recess. Where no sleeve is employed, the frusto-conically tapered internal recess will comprise the inter-engaging part for engagement with the complementary inter-engaging part of the femoral stem. In this embodiment, the anti-rotational element may be provided on one or both of the frusto-conical taper and the frusto-conically tapered recess of the head.

In embodiments, where a femoral sleeve is employed, there may be no need for a further anti-rotational element between an outer surface of the femoral sleeve and the internal recess of the head because there does not, at present, appear to be a problem with this interface (presumably because it has a larger surface area which is better able to resist rotation). However, in certain embodiments of the invention, further anti-rotational elements may be employed at this junction.

One or more of the frusto-conical taper, the frusto-conically tapered recess/passageway of the sleeve or the frusto-conically tapered recess of the head may be off-set such that longitudinal axes of the respective tapers are not aligned when the components are engaged.

In one embodiment, the sleeve is asymmetrical such that the centre of the tapered recess/passageway is off-set with respect to the centre of the sleeve. Accordingly, the sleeve will be thicker on one side of the recess/passageway when compared to the opposite of the recess/passageway.

Where the anti-rotational element comprises a plurality of protuberances in the form of planar surfaces or longitudinal ridges, grooves or splines, it will be possible to dial the sleeve onto the stem in a number of orientations to suit different conditions. As an example, consider the case where a trial symmetric sleeve may be suitable in terms of leg length but may not restore the desired head to stein offset (i.e. the distance between the centre of the head and the longitudinal axis of the stem), and a longer symmetric sleeve may restore the offset but may make the leg too long. A longer asymmetric sleeve can be used in this situation and by dialing the thin side superiorly and the thick side inferiorly the offset can be restored without making the patient's leg too long. Furthermore, if anteversion of the femoral neck is too great, as is found in developmental dysplasia, then the effective femoral neck anteversion can be reduced by dialing the thin side of the sleeve onto the anterior surface of the prosthetic femoral neck. If anteversion of the prosthetic neck is too small, as is found in slipped capital femoral epiphysis, this can be corrected by dialing the thin side of the sleeve onto the posterior surface of the femoral neck thus increasing effective anteversion of the femoral neck. It will therefore be understood that combinations of correction for version, offset and leg length can be achieved by utilizing the equivalent of North-West, South-West, North-East and South-East surfaces on the prosthetic neck. Such surfaces can be provided on a femoral component having a taper with an anti-rotational element in the form of eight flat or grooved surfaces equi-spaced around the axis of the taper. Each flat or grooved surface may include markings to aid a user in orientating an asymmetrical sleeve (including complementary internal flat or ridged surfaces) so as to achieve the desired offset or version.

Clearly an asymmetric sleeve will generate more torque at the inner tapered surfaces and so the anti-rotational element is even more important in these embodiments, in order to ensure that the component is capable of resisting torque.

Where the femoral head fits directly onto the stem, the head may either be symmetric or asymmetric by having the frusto-conically tapered internal recess off-set from the centre of the head. Accordingly, the features described above in relation to asymmetric sleeves are also applicable to asymmetric heads.

The prosthesis may comprise metal, ceramic, polyethylene, or other materials and may be configured for use in a variety of bearing couples (e.g. metal on metal, metal on polyethylene, ceramic on ceramic, ceramic on metal, metal on (PEEK) polyether ether ketone).

According to a third aspect of the present invention there is provided a prosthetic kit comprising a first component and a second component, the first and second components having respective inter-engaging parts, wherein at least one of the first or second components comprises an anti-rotational element configured to resist rotational movement between the inter-engaging parts and wherein the inter-engaging parts share an axis of rotation such that they are engageable in a plurality of relatively rotated positions and wherein the axis of rotation of the inter-engaging part of one of the first or second components is parallel to but offset front a central axis of said first or second component and wherein at least one alternative first or second component is provided having at least one dimension that is different from the respective first or second components.

In embodiments of the present invention, a plurality of sleeves or heads may be provided, each having differing amounts of asymmetry and/or length so as to allow the surgeon to fine tune all the components of offset, version and leg length. For example, it is possible to add to leg length without adding to offset by ensuring the thin side of an asymmetric sleeve/head is located inferiorly on the prosthetic neck.

BRIEF DESCRIPTION OF THE DRAWINGS

Specific embodiments of the present invention are described in more detail below with reference to the accompanying drawings, in which:

FIG. 2A shows a longitudinal cross-sectional view of a symmetrical prosthetic femoral sleeve component for a THR procedure;

FIG. 2B shows an end view of the sleeve of FIG. 2A;

FIG. 2C shows an enlarged end view of a portion of the inner passageway through the sleeve of FIGS. 2A and 2B;

DETAILED DESCRIPTION OF CERTAIN EMBODIMENTS

Figure 1A:
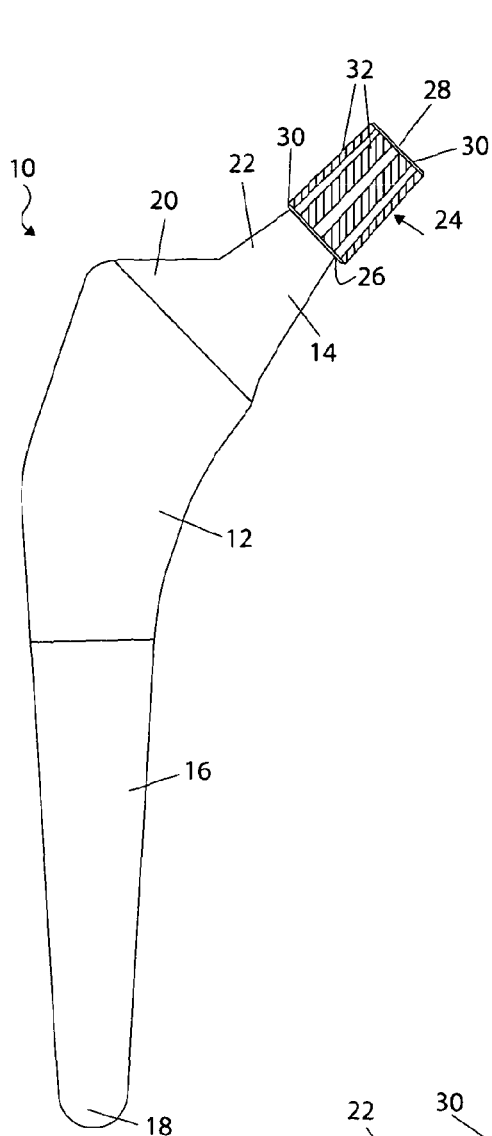
FIG. 1A shows a side view of a prosthetic femoral stem component for a THR procedure, in accordance with an embodiment of the present invention.
Figure 1C:
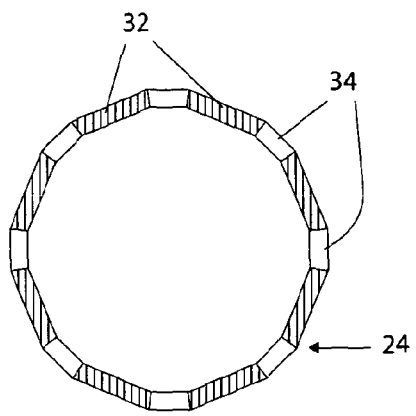
FIG. 1C shows an enlarged transverse cross-sectional view of the inter-engaging portion included in FIGS. 1A and 1B.
Figure 1B:
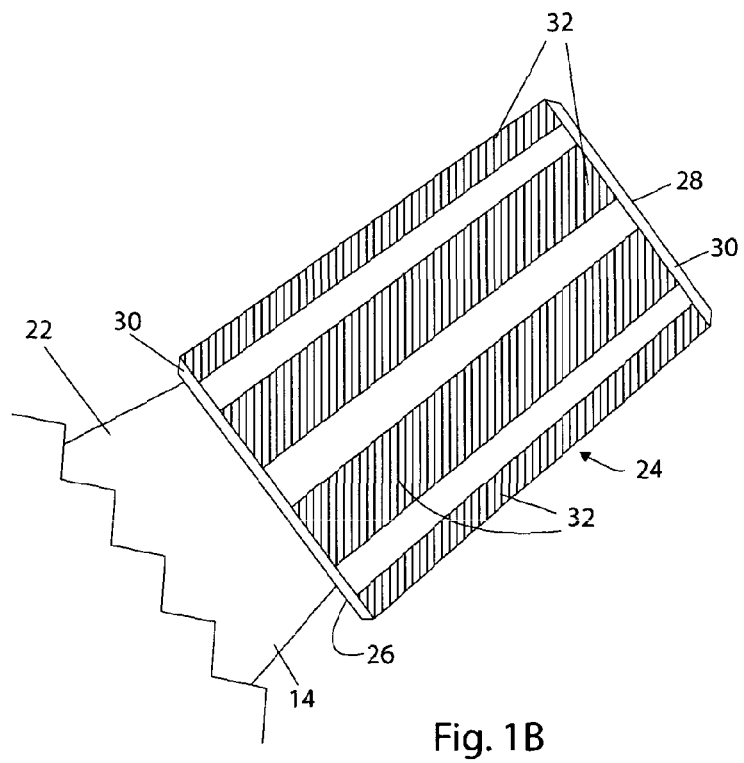
FIG. 1B shows an enlarged side view of the inter-engaging portion extending from the neck of the stem of FIG. 1A.

With reference to FIGS. 1A, 1B and 1C there is illustrated a prosthetic femoral stem component 10 for a THR procedure according to a first embodiment of the present invention. The stem 10 comprises a shoulder 12, a neck 14 and a leg 16. The shoulder 12 has a slightly curved form, tapering inwardly in a distal direction to the most proximal end of the leg 16. The leg 16 comprises a straight elongate conical section tapering inwardly in a distal direction and terminating in a rounded tip 18. The neck 14 extends from the widest and most proximal end of the shoulder 12 and comprises a base 20 and a cone 22. The base 20 tapers more in a lateral direction than in a proximal direction, while the cone 22 comprises a frusto-conical taper extending in a proximal-lateral direction.

An inter-engaging portion 24 is provided at a free end of the cone 22 of the neck 14 for engagement in a prosthetic femoral head or a prosthetic femoral sleeve, as will be described in more detail below. The inter-engaging portion 24 is generally frusto-conical and tapers from a 14 mm diameter base 26 to a 12 mm diameter planar top 28. In other embodiments the taper may go from 12 mm to 10 mm, 16 mm to 14 mm or any other suitable dimensions. As best shown in FIG. 1B, a small chamfer 30 may be provided adjacent the base 26 and the top 28. It will be noted that in the present embodiment, the base 26 is slightly wider than the free end of the cone 22.

An anti-rotational element is provided on the inter-engaging portion 24 in the form of eight non-connected longitudinal flat sections 32 spaced symmetrically around the axis of the taper. For reasons of clarity, hatching is used in FIGS. 1A through 1B to indicate the presence of the flat sections 32. As best shown in FIG. 1C, in this embodiment, the flat sections 32 are machined into the frusto-conical surface of the inter-engaging portion 24 so as to leave curved surfaces 34 protruding there-between. This is advantageous because it will allow the inter-engaging portion 24 to be engaged in either a completely complementary-shaped recess or a simple curved frusto-conical recess (i.e. not including matching flat surfaces).

With reference to FIGS. 2A, 2B and 2C there is illustrated a prosthetic femoral sleeve component 40 for use with the femoral stem 10 of FIG. 1. The sleeve 40 comprises a frusto-conical collar 42 having an inter-engaging portion in the form of a substantially frusto-conically tapering internal passageway 44.

An anti-rotational element is provided on the inter-engaging portion of the sleeve 40, in the form of eight non-connected longitudinal flat sections 46 spaced symmetrically around the axis X of the tapering passageway 44. As above, hatching is used in FIG. 2A to indicate the presence of the flat sections 46. As shown in FIG. 2B, the axis X of the tapering passageway 44 is co-incident with the centre of the sleeve 40. As best shown in FIG. 2C, in this embodiment, the flat sections 46 are interspersed with curved surfaces 48.

Figures 3A, 3B:
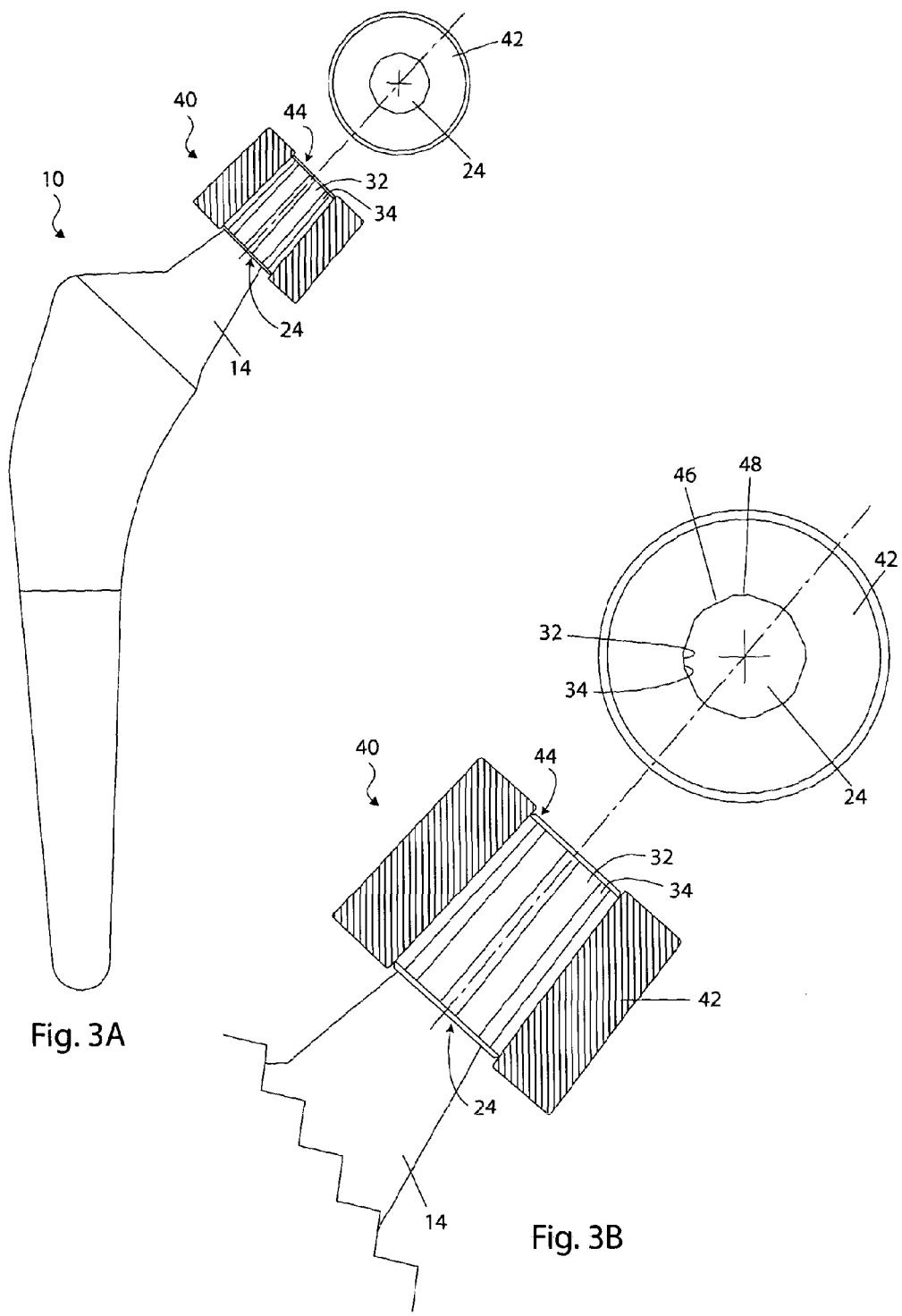
FIG. 3A shows a side cross-sectional view and an associated end view of the stem of FIG. 1A when the sleeve of FIGS. 2A through 2C is engaged therewith.
FIG. 3B shows an enlarged side cross-sectional view and associated end view of the inter-engaging components shown in FIG. 3A.

FIGS. 3A and 3B show the stem 10 of FIG. 1A fitted with the sleeve 40 of FIGS. 2A and 2B. In this case, the cross-section through the sleeve 40 is shown in hatched lines. The sleeve 40 is located on the inter-engaging portion 24 of the neck 14 such that the flat sections 32 and curved sections 34 of the inter-engaging portion 24 mate with the corresponding flat sections 46 and curved sections 48 provided in the passageway 44 of the collar 42. The tapering of the inter-engaging portion 24 and the passageway 44 is such that a tight frictional fit results when the two components are engaged. In addition, the mating flat surfaces 46 and 32 provide resistance to (and may eliminate entirely) relative rotational movement between the sleeve 40 and stem 10, thus, reducing the likelihood of wear and corrosion at this interface.

Figures 4A, 4B:
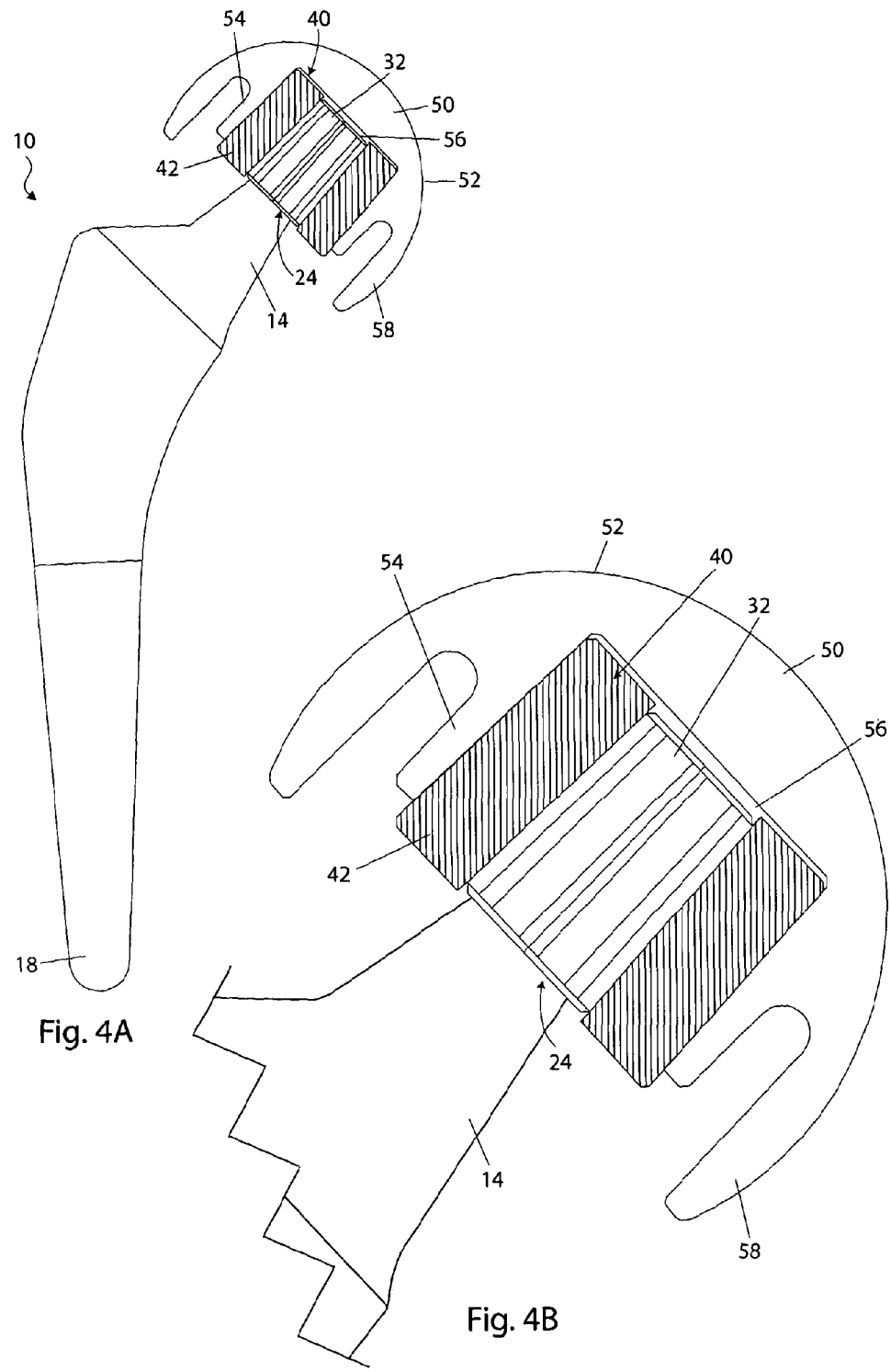
FIG. 4A shows a side cross-sectional view of the components of FIGS. 3A and 3B when fitted with a femoral head.
FIG. 4B shows an enlarged side cross-sectional view of the assembly of FIG. 4A.

In FIGS. 4A and 4B the assembly of FIGS. 3A and 3B is fitted with a prosthetic femoral head component 50. The head 50 comprises a part-spherical exterior bearing surface 52 (configured for location within a corresponding acetabular cup, not shown) and an internal support 54 having a substantially frusto-conically tapered internal recess 56 into which the sleeve 40 is received. The head 50 also includes a skirt 58 depending from the bearing surface 52. The skin 58 is spaced from the support 54 to allow the skirt 58 to be placed over a portion of a patient's resected femur to locate the head 50 thereon.

In use, the stem 10 will first be inserted (tip 18 first) into the medullary canal of a patient's femur, after the femur has been resected at the distal end of the femoral neck. As the stem 10 is generally tapered such that its sides gradually converge from a wider proximal end to a narrower distal end the stem 10 is able to fill the majority of the medullary canal as the femur gradually narrows in a distal direction and this helps to anchor the implant in the femur. The sleeve 40 will then be located on the inter-engaging portion 24 of the neck 14 of the stem 10 so that the respective flat surfaces 46 and 32 engage. The head 50 will then be located on the femur by inserting the sleeve 40 into the recess 56.

When load is applied to the knee joint, frictional torque may be experienced at the bearing interface between the head 50 and the acetabular cup (not shown). However, the provision of the anti-rotational flat surfaces 32, 46 between the stem 10 and the sleeve 40 will prevent this torque from causing relative rotational movement between the components, thereby minimising wear and corrosion.

In embodiments where no sleeve 40 is employed, the head 50 will essentially include the components of the sleeve 40 within the support 54. In other words, the sleeve 40 will be integrated into the head 50 so that the head 50 can be located directly onto the stem 10.

Figure 5A:
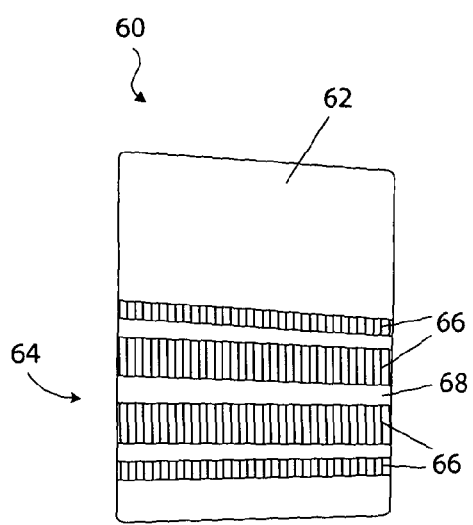
FIG. 5A shows a longitudinal cross-sectional view of an asymmetrical prosthetic femoral sleeve component for a THR procedure, in accordance with an embodiment of the present invention.
Figure 5B:
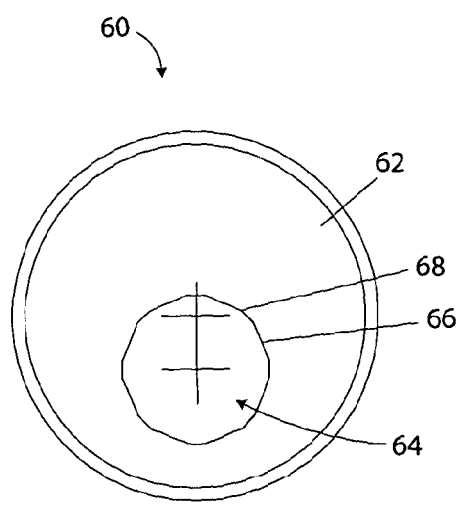
FIG. 5B shows an end view of the sleeve of FIG. 5A.

FIGS. 5A and 5B show an alternative sleeve 60 for use with the femoral stem 10 of FIG. 1. The sleeve 60 is similar to that shown in FIGS. 2A and 2B as it comprises a frusto-conical collar 62 having an inter-engaging portion in the form of a substantially frusto-conically tapering internal passageway 64. In addition, an anti-rotational element is provided on the inter-engaging portion of the sleeve 60, in the form of eight non-connected longitudinal flat sections 66 spaced symmetrically around an axis X of the tapering passageway 64. As above, hatching is used in FIG. 5A to indicate the presence of the flat sections 66. As for the sleeve 40, the flat sections 66 in this embodiment are interspersed with curved surfaces 68. However, unlike in the sleeve 40, the axis X of the tapering passageway 64 is not co-incident with the centre X' of the sleeve 60. Instead, the axis X of the tapering passageway 64 is parallel to the central axis X' but off-set to one side (by 4 mm) when measured from the centre X' of the sleeve 60, so as to create an asymmetrical sleeve 60.

Figures 6A, 6B:
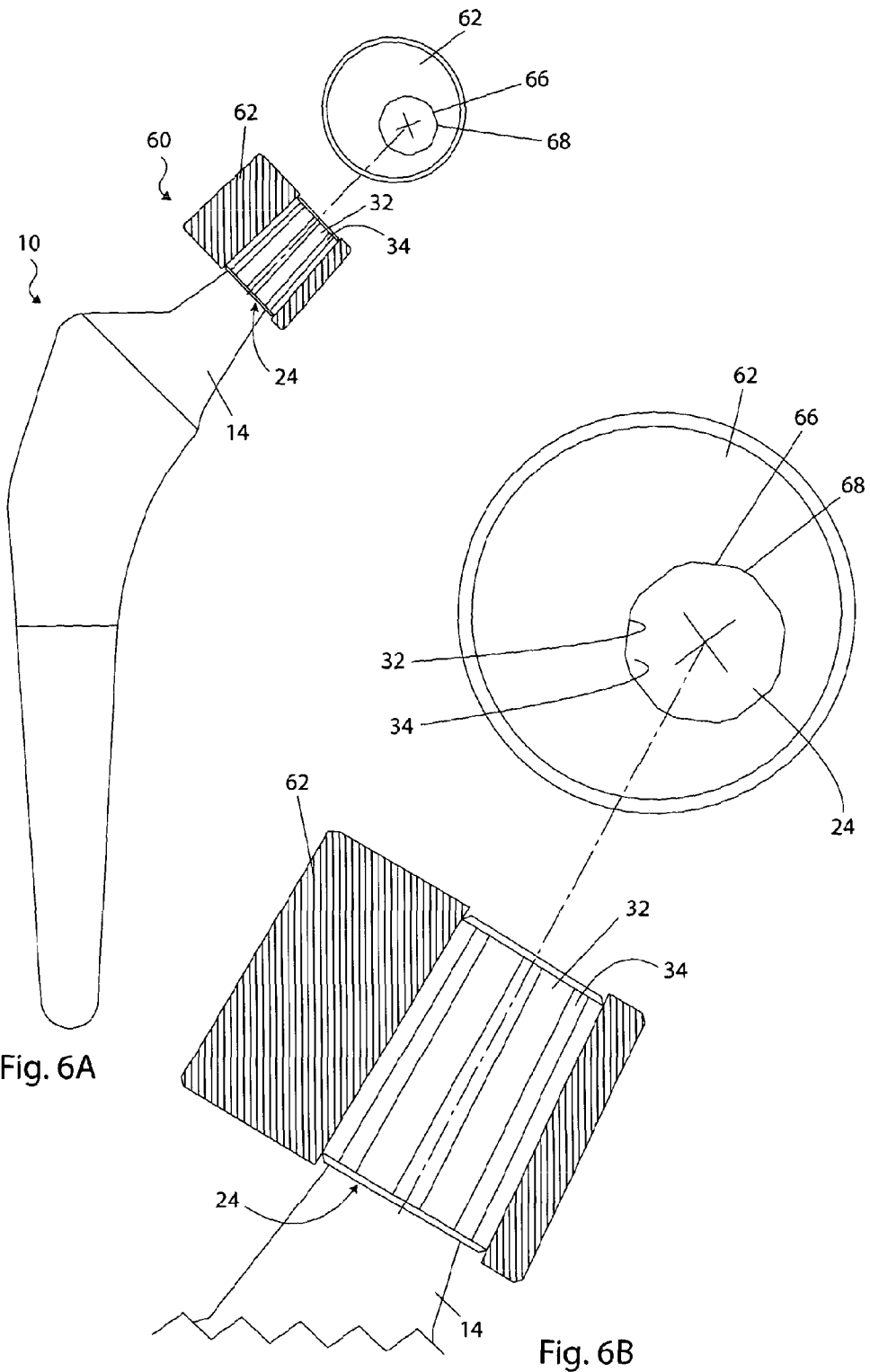
FIG. 6A shows a side cross-sectional view and an associated end view of the stem of FIG. 1A when the sleeve of FIGS. 5A and 5B is engaged therewith, in accordance with an embodiment of the present invention.
FIG. 6B shows an enlarged side cross-sectional view and associated end view of the inter-engaging components shown in FIG. 6A.

FIGS. 6A and 6B show the stem 10 of FIG. 1A fitted with the asymmetrical sleeve 60 of FIGS. 5A and 5B. The cross-section through the sleeve 60 is shown in hatched lines. The sleeve 60 is located on the inter-engaging portion 24 of the neck 14 such that the flat sections 32 and curved sections 34 of the inter-engaging portion 24 mate with the corresponding flat sections 66 and curved sections 68 provided in the passageway 64 of the collar 62. As previously described, the tapering of the inter-engaging portion 24 and the passageway 64 is such that a tight frictional fit results when the two components are engaged. In addition, the mating flat surfaces 66 and 32 provide resistance to (and may eliminate entirely) relative rotational movement between the sleeve 60 and stem 10, thus, reducing the likelihood of wear and corrosion at this interface.

Figure 7:
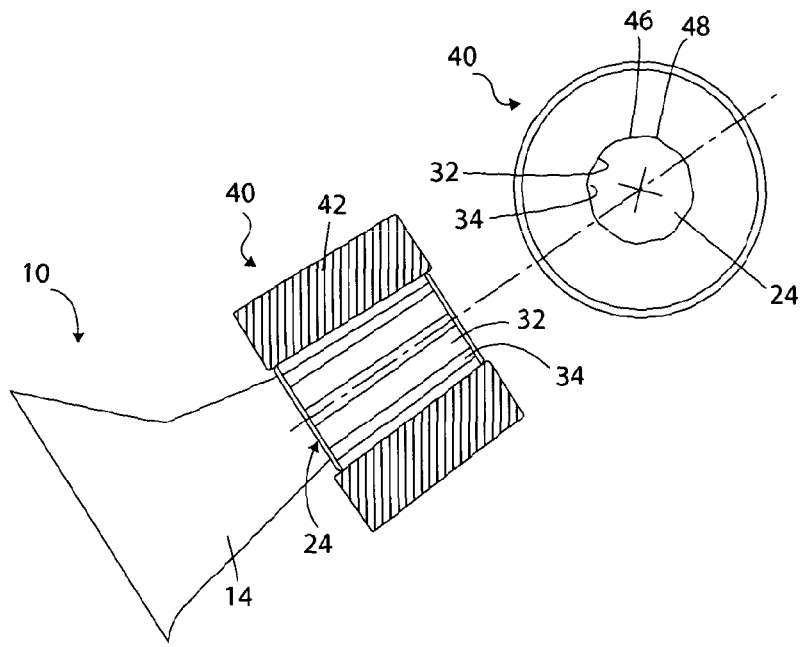
FIG. 7 shows a view similar to that shown in FIG. 3B comprising an enlarged side cross-sectional view and associated end view of the inter-engaging components when the symmetrical sleeve (of FIGS. 2A through 2C) is engaged with the stem.

FIG. 7 shows a view similar to that shown in FIG. 3B showing the inter-engaging components when the symmetrical sleeve 40 of FIGS. 2A through 2C is engaged with the stem 10. Regardless of which of the flat sections 32, 46 and curved sections 34, 48 are placed adjacent each other, the end view of the sleeve 40 on the stem 10 is always in the same relative position due to the symmetrical (or neutral) nature of the sleeve 40.

Figure 8:
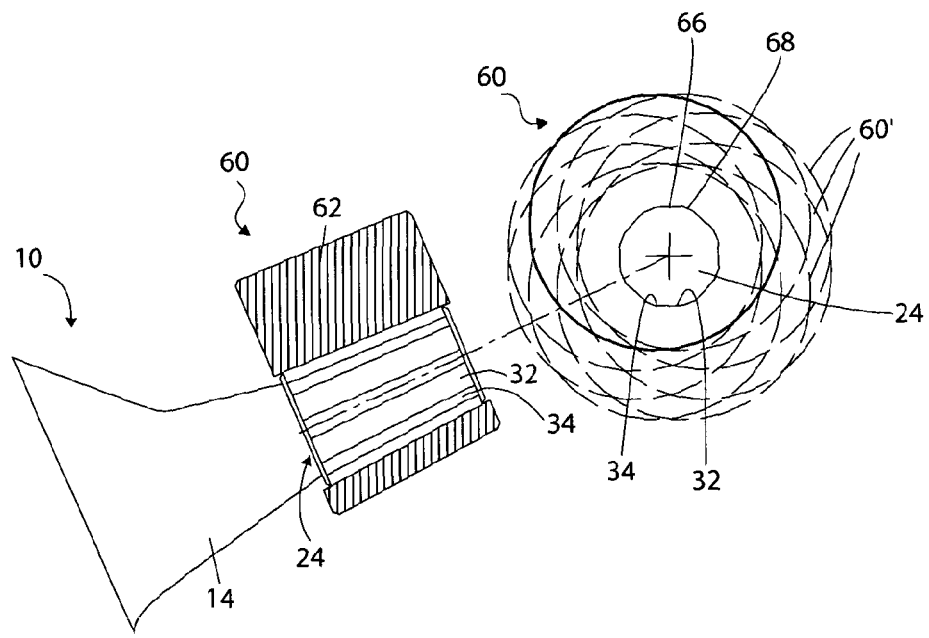
FIG. 8 shows a view similar to that shown in FIG. 6B comprising an enlarged side cross-sectional view and associated end view of the inter-engaging components when the asymmetrical sleeve (of FIGS. 5A and 5B) is engaged with the stem, and wherein the a series of dashed lines is shown illustrate the range possible relative positions of the sleeve on the stem.

For comparison, FIG. 8 shows a view similar to that shown in FIG. 6B showing the inter-engaging components when the asymmetrical sleeve 60 of FIGS. 5A and 5B is engaged with the stem 10. In this case, the relative position of the sleeve 60 on the stem 10 varies depending on the orientation of the sleeve 60 when it is engaged on the inter-engaging part 24. Dashed lines 60' represent possible positions for the sleeve 60 when viewed end on. By rotating (i.e. dialing) the sleeve 60 so that the flat surfaces 66 of the sleeve 60 are positioned adjacent the next set of flat surfaces 32 on the inter-engaging component 24, the sleeve 60 can be stepped around the neck 14 of the stem 10 so that the thickest and thinnest portions of the collar 62 are re-positioned in order to provide the desired degree of version and off-set of the head 50 (not shown) with respect to the stem 10. Consequently, fewer different sized components are required to be stocked in order to suit a range of different circumstances.

Figures 9, 10:
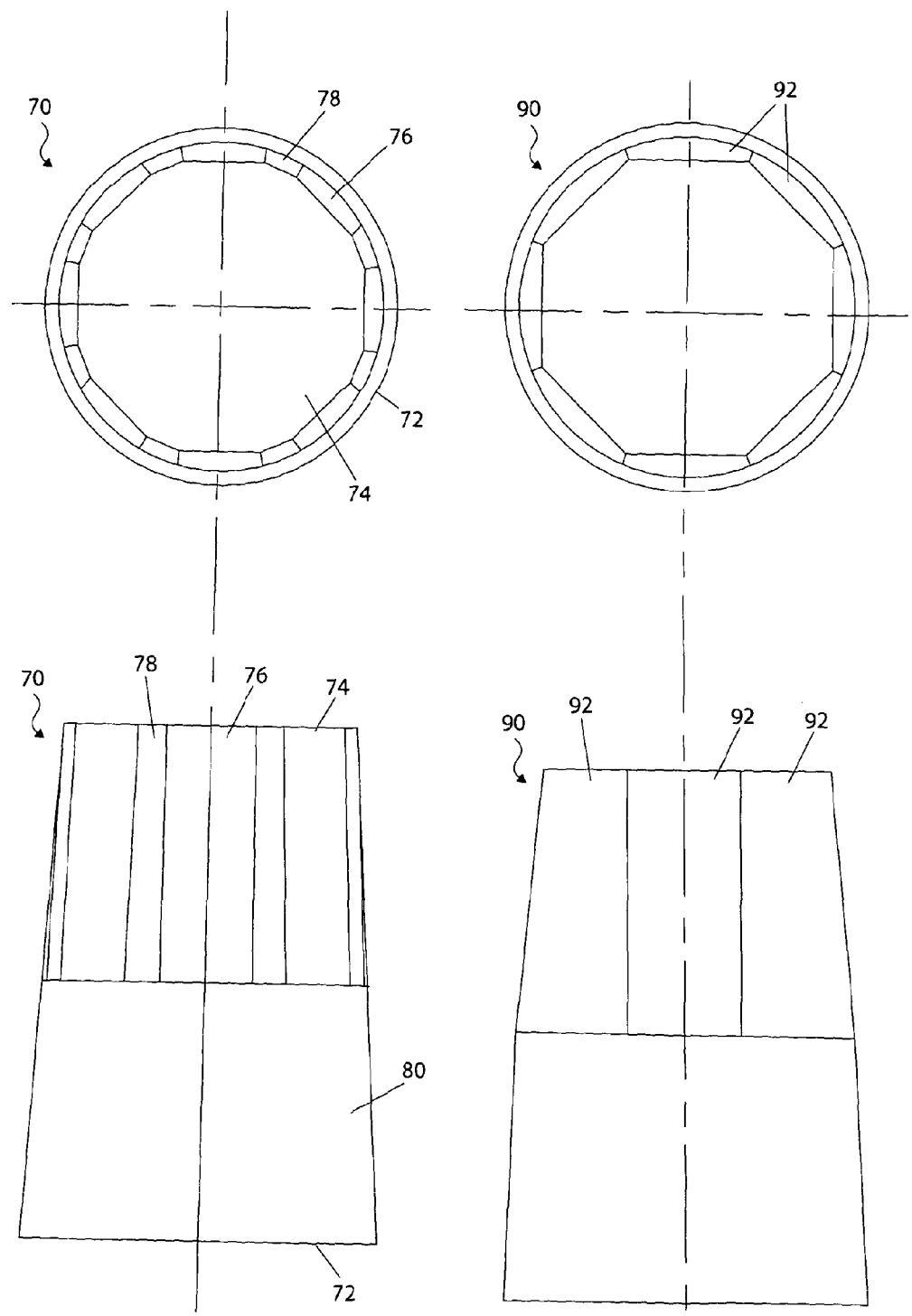
FIG. 9 shows a side view and an associated end view of an alternative inter-engaging portion for the stem of FIG. 1A, according to an embodiment of the invention.
FIG. 10 shows a side view and an associated end view of a further inter-engaging portion for the stem of FIG. 1A, according to an embodiment of the invention.

FIG. 9 shows a side view and an associated end view of an alternative inter-engaging portion 70 for the stem 10 of FIG. 1A, according to an embodiment of the invention. The inter-engaging portion 70 is similar to the inter-engaging portion 24 of FIG. 1A in that it is generally frusto-conical and tapers from a 14 mm diameter base 72 to a 12 mm diameter planar top 74. In addition, an anti-rotational element is provided on the inter-engaging portion 70 in the form of eight non-connected longitudinal flat sections 76 spaced symmetrically around the axis of the taper. As before, the flat sections 76 are machined into the frusto-conical surface of the inter-engaging portion 70 so as to leave curved surfaces 78 protruding there-between. However, unlike the inter-engaging portion 24, the anti-rotational element on the inter-engaging portion 70 is only present in the upper (narrower) half of the tapered surface. Accordingly, the lower (thicker) half of the inter-engaging portion 70 comprises a smooth curved surface 80 which is continuous with the curved surfaces 78. This provides a greater surface area for use with a femoral sleeve or head not including flat anti-rotational elements.

FIG. 10 shows a side view and an associated end view of a further inter-engaging portion 90 for the stem 10 of FIG. 1A, according to an embodiment of the invention. The inter-engaging portion 90 is similar to that shown in FIG. 9 except that, in the present case, the eight flat surfaces 92 forming the anti-rotational element are connected to form an octagonal cone in the upper (narrower) half of the tapered surface.

A further embodiment of the present invention (not shown) is similar to that shown in FIG. 10 but wherein the eight connected flat surfaces are provided over the entire length of the inter-engaging portion so as to form an octagonal cone over the whole of the tapered surface.

Figure 11:
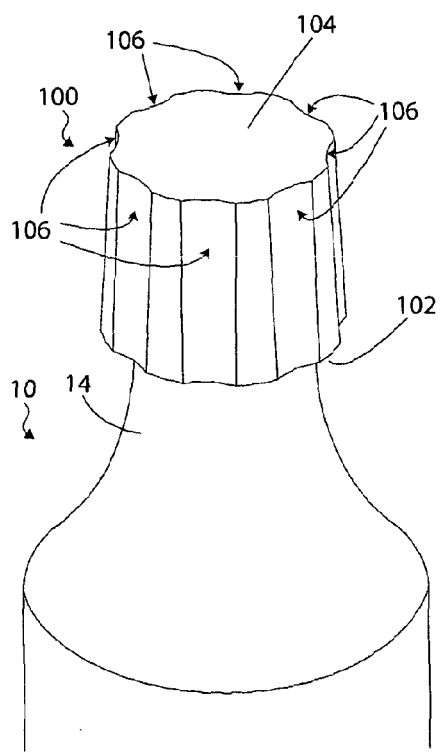
FIG. 11 shows a side perspective view of a further inter-engaging portion for the neck of the stem shown in FIG. 1A, in accordance with another embodiment of the present invention.

FIG. 11 shows a side perspective view of a further inter-engaging portion 100 for the neck 14 of the stem 10 shown in FIG. 1A, in accordance with another embodiment of the present invention. The inter-engaging portion 100 is similar to the inter-engaging portion 24 of FIG. 1A in that it is generally frusto-conical and tapers from a 14 mm diameter base 102 to a 12 mm diameter planar top 104. In addition, eight non-connected anti-rotational elements 106 are provided on the inter-engaging portion 100 and are spaced symmetrically around the axis of the taper. However, in this embodiment, each anti-rotational element 106 is in the form of a longitudinal concavely curved channel. As before, the anti-rotational elements 106 are machined into the frusto-conical surface of the inter-engaging portion 100 so as to leave convexly curved surfaces 108 protruding there-between so as to allow the inter-engaging portion 100 to be engaged in either a completely complementary-shaped recess or a simple concavely curved frusto-conical recess (i.e. not including matching convexly curved protrusions to mate with the concavely curved channels 106).

Figure 12:
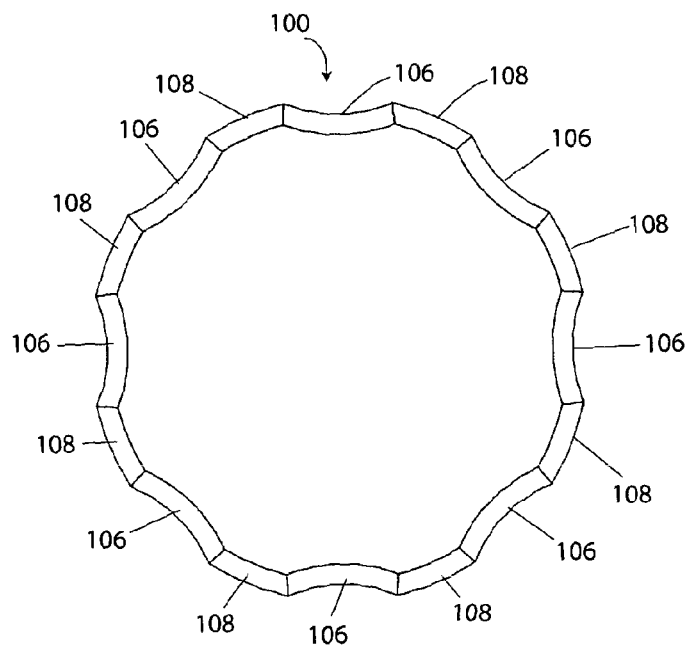
FIG. 12 shows a transverse cross-sectional view through the inter-engaging portion of the neck of FIG. 11.

As best shown in FIG. 12, the anti-rotational elements 106 form deeper curves than the intervening convexly curved surfaces 108. This helps to ensure that the anti-rotational elements 106 only allow insertion of a sleeve/head having a complementary shaped recess/passageway when it is correctly aligned with the anti-rotational elements 106 and also helps to ensure that relative rotational movement is resisted when the components are engaged. Furthermore, it is clearly shown in FIG. 12 that the outer surface of the inter-engaging portion 100 has alternately inwardly and outwardly curved regions forming a rippled circumference.

Figure 13:
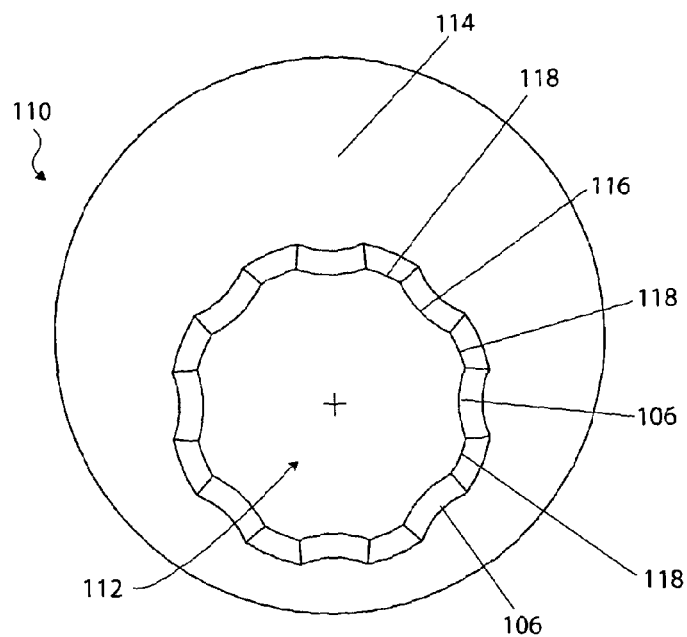
FIG. 13 shows a bottom view of a sleeve including an inter-engaging portion configured to mate with the neck of FIG. 11.

FIG. 13 shows a bottom view of a sleeve 110 having an offset inter-engaging passageway 112 configured to mate with the inter-engaging portion 100 of FIG. 11. The sleeve 110 comprises a frusto-conical collar 114 housing the inter-engaging passageway 112 which is substantially frusto-conically tapering inwardly in an upwardly direction. In addition, eight non-connected anti-rotational elements 116 are provided on the inter-engaging passageway 112, in the form of eight longitudinal convexly curved protrusions or ridges which are spaced symmetrically around an axis X of the tapering passageway 112. As for the sleeve 40, the convexly curved protrusions 116 in this embodiment are interspersed with concavely curved surfaces 118. However, unlike in the sleeve 40, the axis X of the tapering passageway 112 is not co-incident with the centre of the sleeve 110. Instead, the axis X of the tapering passageway 112 is off-set to one side by approximately 4 mm when measured from the centre of the sleeve 110, so as to create an asymmetrical sleeve 110.

Figure 14:
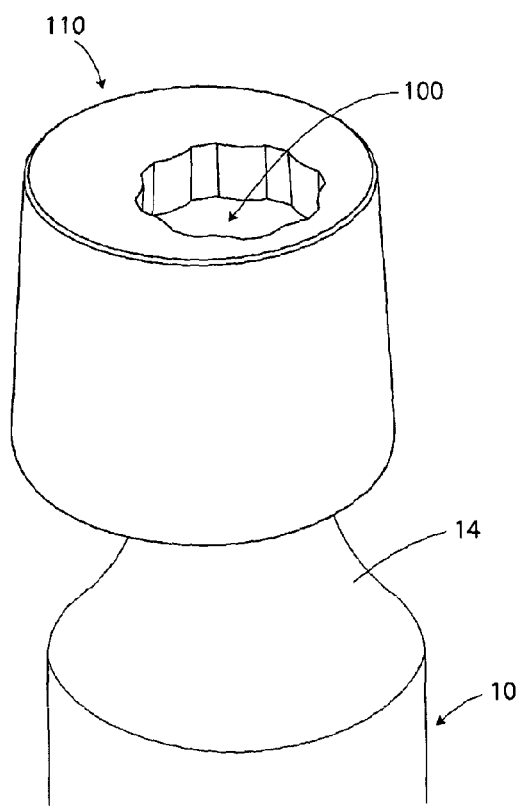
FIG. 14 shows a side perspective view of the neck of FIG. 11 when fitted with the sleeve of FIG. 13.

FIG. 14 shows a side perspective view of the neck 14 of FIG. 11 when fitted with the sleeve 110 of FIG. 13. More specifically, the sleeve 110 is located on the inter-engaging portion 100 of the neck 14 such that the concavely curved sections 106 and the convexly curved sections 108 of the inter-engaging portion 100 mate with the corresponding convexly curved protrusions 116 and concavely curved sections 118 provided in the passageway 112 of the collar 110. As previously described, the tapering of the inter-engaging portion 100 and the passageway 112 is such that a tight frictional fit results when the two components are engaged. In addition, the curved mating surfaces 106 and 116 provide resistance to (and may eliminate entirely) relative rotational movement between the sleeve 110 and stem 10, thus, reducing the likelihood of wear and corrosion at this interface.

It will be appreciated by persons skilled in the art that various modifications may be made to the above embodiments without departing from the scope of the present invention.

The invention claimed is:

1. A hip prosthesis comprising a first component configured as a femoral stem and neck and a second component configured as either a femoral sleeve or a femoral head for securement on the femoral neck,
    wherein the femoral neck comprises a tapered surface which tapers in a proximal direction from a 14 mm diameter circular cross-section to a 12 mm diameter circular cross-section and at least four longitudinal grooves are machined along a whole or a portion of the tapered surface;
    wherein the longitudinal grooves are symmetrically spaced apart around a circumference of the tapered surface;
    wherein the second component comprises a complementary tapered recess and longitudinal elements for selective engagement in said longitudinal grooves; and
    wherein an axis of rotation of the femoral neck is parallel to but offset from a central axis of said second component when secured thereon.

2. The hip prosthesis according to claim 1 wherein the longitudinal grooves comprise planar surfaces.

3. A prosthetic kit comprising:
    a hip prosthesis comprising a first component configured as a femoral stem and neck and a second component configured as either a femoral sleeve or a femoral head for securement on the femoral neck,
    wherein the femoral neck comprises a tapered surface which tapers in a proximal direction from a 14 mm diameter circular cross-section to a 12 mm diameter circular cross-section and at least four longitudinal grooves are machined along a whole or a portion of the tapered surface;
    wherein the longitudinal grooves are symmetrically spaced apart around a circumference of the tapered surface;
    wherein the second component comprises a complementary tapered recess and longitudinal elements for selective engagement in said longitudinal grooves; and
    wherein an axis of rotation of the femoral neck is parallel to but offset from a central axis of said second component when secured thereon; and
    at least one alternative first or second component having at least one dimension that is different from the respective first or second components of said hip prosthesis.

4. The prosthetic kit according to claim 3 wherein a plurality of femoral sleeves or femoral heads is provided, each having differing amounts of asymmetry and/or length so as to allow offset, version and/or leg length to be adjusted.

* * * * *